(12) United States Patent  
Watanabe et al.

(10) Patent No.: US 9,326,740 B2  
(45) Date of Patent: May 3, 2016

(54) RADIOGRAPHIC SYSTEM

(71) Applicants:Kabushiki Kaisha Toshiba, Minato-ku (JP); Toshiba Medical Systems Corporation, Otawara-shi (JP)

(72) Inventors: Takahito Watanabe, Nasushiobara (JP); Hideo Saito, Nasushiobara (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 142 days.

(21) Appl. No.: 14/345,577

(22) PCT Filed: Aug. 6, 2013

(86) PCT No.: PCT/JP2013/071252  
§ 371 (c)(1),  
(2) Date: Mar. 18, 2014

(87) PCT Pub. No.: WO2014/024881  
PCT Pub. Date: Feb. 13, 2014

(65) Prior Publication Data  
US 2014/0348289 A1 Nov. 27, 2014

(30) Foreign Application Priority Data

Aug. 7, 2012 (JP) ................................ 2012-175344  
Aug. 5, 2013 (JP) ................................ 2013-162588

(51) Int. Cl.  
*A61B 6/03* (2006.01)  
*H05G 1/34* (2006.01)  
(Continued)

(52) U.S. Cl.  
CPC ................. *A61B 6/405* (2013.01); *A61B 6/032* (2013.01); *A61B 6/40* (2013.01); *A61B 6/54* (2013.01);  
(Continued)

(58) Field of Classification Search  
CPC .......... A61B 6/032; A61B 6/40; A61B 6/405; A61B 6/54; A61B 6/542; A61B 6/545; A61B 6/582; A61B 6/586; H05G 1/265; H05G 1/30; H05G 1/32; H05G 1/34  
USPC .................................... 378/16, 108, 109, 110  
See application file for complete search history.

(56) References Cited

U.S. PATENT DOCUMENTS

| 3,766,391 A | * | 10/1973 | Siedband | ................. | H05G 1/34 |
| | | | | | 315/302 |
| 4,035,649 A | * | 7/1977 | Mester | ..................... | H05G 1/46 |
| | | | | | 378/108 |

(Continued)

FOREIGN PATENT DOCUMENTS

| JP | 9 161990 | 6/1997 |
| JP | 2000 260594 | 9/2000 |

(Continued)

OTHER PUBLICATIONS

International Search Report Issued Sep. 10, 2013 in PCT/JP13/071252 filed Aug. 6, 2013.

*Primary Examiner* — Allen C. Ho  
(74) *Attorney, Agent, or Firm* — Oblon, McClelland, Maier & Neustadt, L.L.P.

(57) ABSTRACT

A radiographic system is provided that can shorten the work time required for adjusting the initial values. The radiographic system comprises: an X-ray tube controller; an initial value calculator; and a storage. The X-ray tube controller is configured to control a filament current flowing through a filament of the X-ray tube for stabilizing the tube current at a desired value, the tube current otherwise tending to fluctuate at activation. The initial value calculator is configured to calculate an initial value for the filament current that is to be applied at next activation, based both on a stable value of the filament current while the tube current has been stable and on the image-capturing conditions at the time. The storage configured to store the calculated initial value, the image-capturing conditions, and a radiographic history that includes radiographed dates.

9 Claims, 13 Drawing Sheets

(51) Int. Cl.
*A61B 6/00* (2006.01)
*H05G 1/30* (2006.01)
*H05G 1/26* (2006.01)
*H05G 1/32* (2006.01)

(52) U.S. Cl.
CPC .............. *A61B 6/542* (2013.01); *A61B 6/545* (2013.01); *A61B 6/582* (2013.01); *H05G 1/265* (2013.01); *H05G 1/30* (2013.01); *H05G 1/32* (2013.01); *H05G 1/34* (2013.01); *A61B 6/586* (2013.01)

(56) References Cited

U.S. PATENT DOCUMENTS

| | | | | |
|---|---|---|---|---|
| 4,177,406 A * | 12/1979 | Hermeyer | H05G 1/34 | 315/106 |
| 4,191,889 A * | 3/1980 | Cowell | H05G 1/34 | 378/109 |
| 4,191,891 A * | 3/1980 | Amtmann | H05G 1/32 | 378/109 |
| 4,322,797 A * | 3/1982 | Lickel | H05G 1/34 | 378/110 |
| 4,346,297 A * | 8/1982 | Suzuki | H05G 1/34 | 315/107 |
| 4,366,575 A * | 12/1982 | Bax | A61B 6/032 | 378/110 |
| 4,377,748 A * | 3/1983 | Aichinger | H05G 1/46 | 378/110 |
| 4,402,086 A * | 8/1983 | Setbon | H05G 1/54 | 378/105 |
| 4,797,907 A * | 1/1989 | Anderton | H05G 1/10 | 378/101 |
| 4,930,145 A * | 5/1990 | Sherwin | H05G 1/32 | 378/109 |
| 5,077,773 A * | 12/1991 | Sammon | H05G 1/46 | 378/109 |
| 5,400,378 A * | 3/1995 | Toth | A61B 6/032 | 378/108 |
| 5,708,694 A * | 1/1998 | Beyerlein | H05G 1/34 | 378/109 |
| 5,867,555 A * | 2/1999 | Popescu | A61B 6/032 | 378/16 |
| 6,094,468 A * | 7/2000 | Wilting | A61B 6/032 | 378/16 |
| 6,198,789 B1 * | 3/2001 | Dafni | A61B 6/032 | 378/15 |
| 6,507,639 B1 * | 1/2003 | Popescu | A61B 6/032 | 378/108 |
| 6,744,846 B2 * | 6/2004 | Popescu | A61B 6/032 | 378/16 |
| 6,775,352 B2 * | 8/2004 | Toth | A61B 6/032 | 378/101 |
| 6,904,127 B2 * | 6/2005 | Toth | A61B 6/032 | 378/108 |
| 6,987,828 B2 * | 1/2006 | Horiuchi | G01N 23/046 | 378/108 |
| 7,103,139 B2 * | 9/2006 | Nagaoka | A61B 6/032 | 378/16 |
| 7,106,824 B2 * | 9/2006 | Kazama | A61B 6/032 | 378/110 |
| 7,203,270 B2 * | 4/2007 | Okumura | A61B 6/032 | 378/109 |
| 7,215,733 B2 * | 5/2007 | Nabatame | A61B 6/032 | 378/110 |
| 7,366,283 B2 * | 4/2008 | Carlson | H05G 1/46 | 378/108 |
| 7,460,635 B2 * | 12/2008 | Fujimoto | A61B 6/032 | 378/16 |
| 7,558,364 B2 * | 7/2009 | Lin | A61B 6/542 | 378/16 |
| 7,636,416 B2 * | 12/2009 | Miyazaki | A61B 6/542 | 378/108 |
| 8,175,217 B2 * | 5/2012 | Sugaya | A61B 6/032 | 378/16 |
| 8,184,768 B2 * | 5/2012 | Honda | A61B 6/032 | 378/134 |
| 8,487,534 B2 * | 7/2013 | Caiafa | H05G 1/32 | 315/111.31 |
| 8,687,763 B2 * | 4/2014 | Feuerlein | A61B 6/032 | 378/110 |
| 8,699,658 B2 * | 4/2014 | Yu | A61B 6/032 | 378/16 |
| 8,744,039 B2 * | 6/2014 | Hirokawa | A61B 6/032 | 378/108 |
| 8,842,805 B2 * | 9/2014 | Proksa | A61B 6/032 | 378/16 |
| 8,848,860 B2 * | 9/2014 | Yazaki | A61B 6/488 | 378/16 |
| 9,125,619 B2 * | 9/2015 | Yabugami | A61B 6/485 | |

FOREIGN PATENT DOCUMENTS

| | | |
|---|---|---|
| JP | 2001 104297 | 4/2001 |
| JP | 2006 120548 | 5/2006 |
| JP | 2008 218338 | 9/2008 |
| JP | 2011 115369 | 6/2011 |

* cited by examiner

RADIOGRAPHIC SYSTEM

TECHNICAL FIELD

Embodiments according to the present invention relate to radiographic systems.

BACKGROUND ART

Here, radiographic systems include diagnostic X-ray apparatuses, which are equipped with an X-ray generator for irradiating the subject with X-rays and acquire tomographic images of the subject, based on the X-rays that have passed through the subject. As an example of diagnostic X-ray apparatus, there is an X-ray CT system configured to radiate X-rays with an X-ray tube that revolves around the body axis of the subject while the subject placed on the top plate of the system is being moved in the rostrocaudal direction. The system acquires CT images of the subject on the basis of the X-rays that have passed through the subject (e.g., patent reference 1).

The X-ray tube, which has a cathode and an anode, is operated in accordance with image-capturing conditions that include the tube voltage and tube current to be applied between the anode and the cathode, as well as X-ray focal spot size. For activation, the X-ray tube is applied with a high voltage, and, as the tube current tends to fluctuate in its rising up, the electric current flowing through the filament of the tube (hereinafter referred to as "filament current") is carefully controlled for stabilizing the tube current at a desired value in order to generate X-rays from the anode at a predetermined output. The filament current rising up and flowing through the cathode when the radiography is started up is referred to as "initial value", and the filament current while the tube current is stable is referred to as "stable value". It is desirable to apply an appropriate initial value for achieving stabilization of the tube current within a very short time.

It is known that the filament of the X-ray tube undergoes aging and that, through the aging, the tube current becomes smaller for the same filament current. Because of this reason, even though the original initial value is appropriate, it becomes not appropriate after use for a long period of time, resulting in that an increasingly longer time is required for the tube current to stabilize.

For stabilizing the tube current in a very short time even after the aging of the filament, the initial value is adjusted for each of the image-capturing conditions by a service engineer when the X-ray CT system is installed or thereafter when it is tested periodically (these occasions are both hereinafter referred to as "at the time of adjustment").

In a conventional method of adjusting the initial value, after X-ray generation is executed under predetermined image-capturing conditions, the output profile obtained is analyzed, and then the initial value of the filament current is modified and adjusted until X-ray outputs settle within a predetermined threshold value.

The initial value is adjusted for each of the points of the tube current predetermined with an increment of, for example, 10 [mA]. If some of the initial values are not actually adjusted, then they are calculated by linear interpolation with the initial values that have been adjusted for other points. The initial values actually adjusted for their corresponding points and the interpolated initial values are stored together in a table format in a storage. The stored initial values are used at the time of a next adjustment. Incidentally, the initial values that are used at the time of a next adjustment may be referred to as "next initial values".

Tables are prepared for combinations of various tube voltages and focal spot sizes applicable. In other words, a table is prepared for each possible setting of the image-capturing conditions. If the X-ray CT system enables four tube voltage settings and two focal spot sizes as image-capturing conditions, then it will be equipped with eight such tables.

Furthermore, in recent years, there has been a tendency that X-ray CT systems are configured to speed up the revolving motion of the X-ray tube for the purpose of broadening their scanning range without increasing the amount of radiation the subject is exposed to. Accordingly, the X-ray generation is directed for an increasingly higher power for prevention of tube current shortage that can be otherwise caused by the increased higher revolving speed of the X-ray tube.

PRIOR ART REFERENCES

Patent References

[Patent Reference 1] Japanese Laid-Open Patent Publication No. 2001-104297

SUMMARY OF THE INVENTION

Problems to be Solved by the Invention

However, there is a problem that as the period from the adjustment of the next initial values to the next adjustment becomes longer, the next initial values tend to become inappropriate. As the degree of inappropriateness increases, longer will the work time be required for adjusting the initial values.

In addition, as the X-ray generation becomes more and more powerful, the number of tube-current values applicable as conditions also becomes correspondingly larger, leading to the increased number of elements that should be provided on the tables. This has led to another problem that the work time required for adjusting the initial values is even becoming longer with the increased number of initial values, which should be adjusted.

The present embodiment is to solve the above-mentioned problems, and its objective is to provide a radiographic system that can shorten the work time required for adjusting the initial values.

Means for Solving the Problems

In order to solve above-mentioned problem, a radiographic system of this embodiment comprises: an X-ray tube controller; an initial value calculator; and a storage. The X-ray tube controller is configured to control a filament current flowing through a filament of the X-ray tube for stabilizing the tube current at a desired value, the tube current otherwise tending to fluctuate at activation. The initial value calculator is configured to calculate an initial value for the filament current that is to be applied at next activation, based both on a stable value of the filament current while the tube current has been stable and on the image-capturing conditions at the time. The storage configured to store the calculated initial value, the image-capturing conditions, and a radiographic history that includes radiographed dates.

BRIEF DESCRIPTION OF THE DRAWINGS

FIG. 2 is a block diagram showing an X-ray tube controller, and so on.

PREFERRED EMBODIMENTS OF THE INVENTION

First Embodiment

Figure 1:
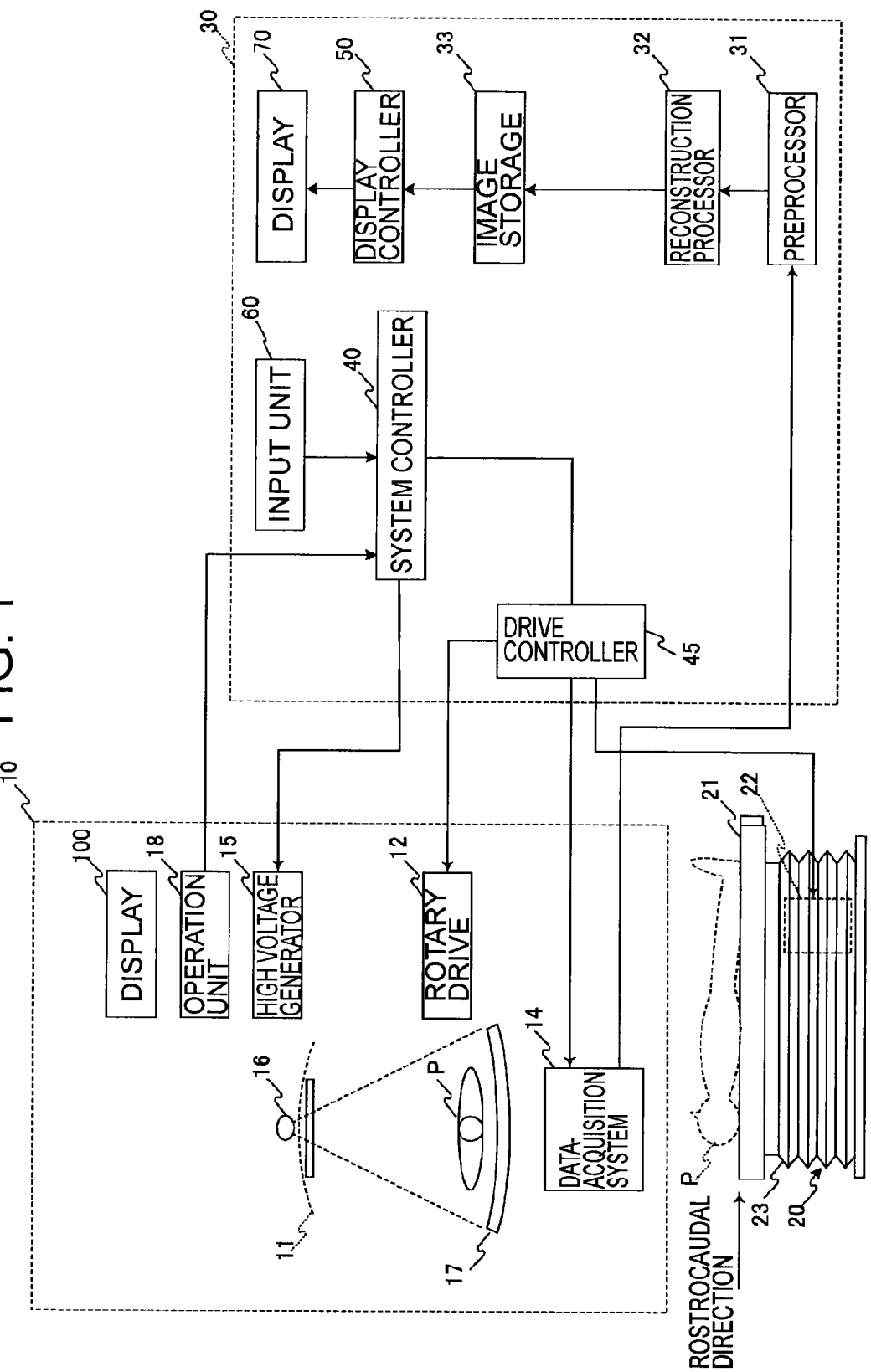
FIG. 1 is a block diagram showing the configuration of an X-ray CT system as a first embodiment.
Figure 2:
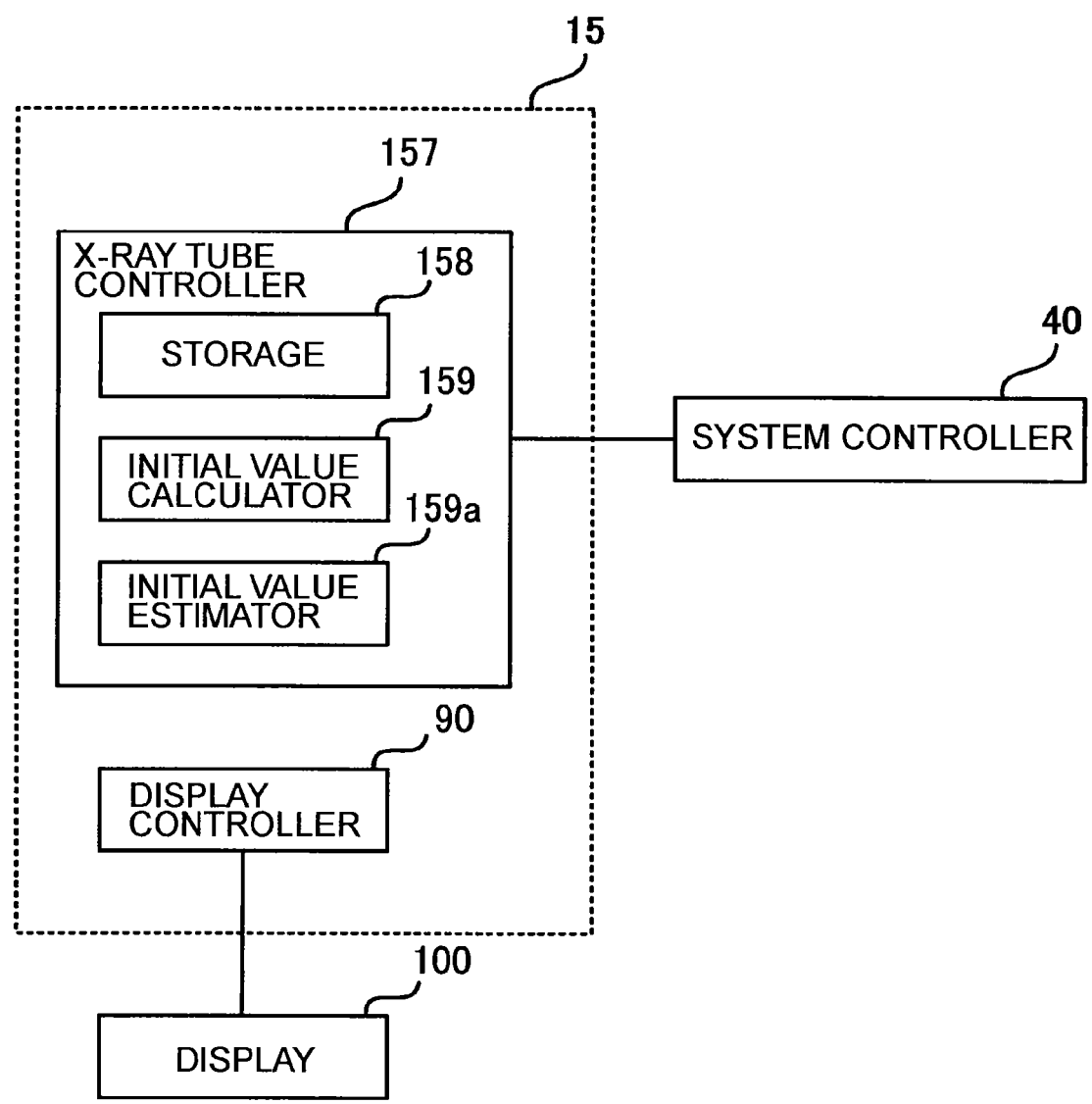

Now, a first embodiment of radiographic system is described with reference to each of the drawings. FIG. 1 is a block diagram showing an X-ray CT system, and FIG. 2 is a block diagram showing an X-ray tube controller. In the following, the X-ray CT system is described as an example of a radiographic system.

As shown in FIG. 1, the X-ray CT system is configured to include a gantry 10, a patient table 20, and a console 30.

Conventionally, next initial values are calculated at the time of adjustment but in this embodiment, an arrangement is made so that next initial values are calculated also at the time of radiography. In the following description, either radiography or adjustment may be referred to as "radiography or the like".

(Gantry)

As shown in FIG. 1, the gantry 10 comprises a high voltage generator 15 and an X-ray tube 16.

Figure 4:
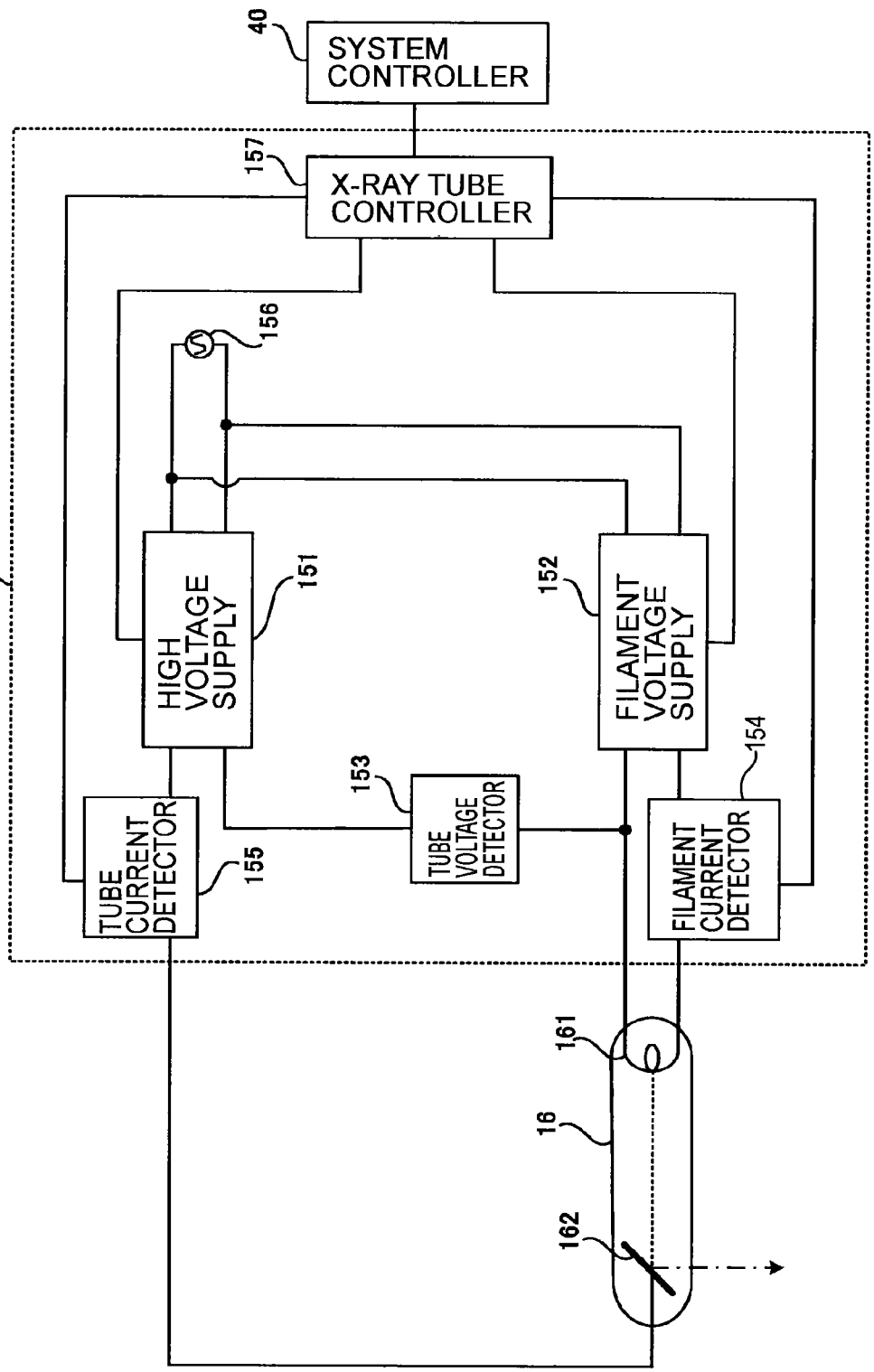
FIG. 4 is a block diagram showing a high voltage generator.

The X-ray tube 16 has a cathode 161 and an anode 162 (refer to FIG. 4). The cathode 161 comprises a filament. In radiography or the like, a tube voltage is applied between the cathode 161 and the anode 162 for activation, and a filament current is made to flow through the filament. As a result, a tube current flows between the cathode 161 and the anode 162, and X-rays are generated at the anode 162.

Figure 3:
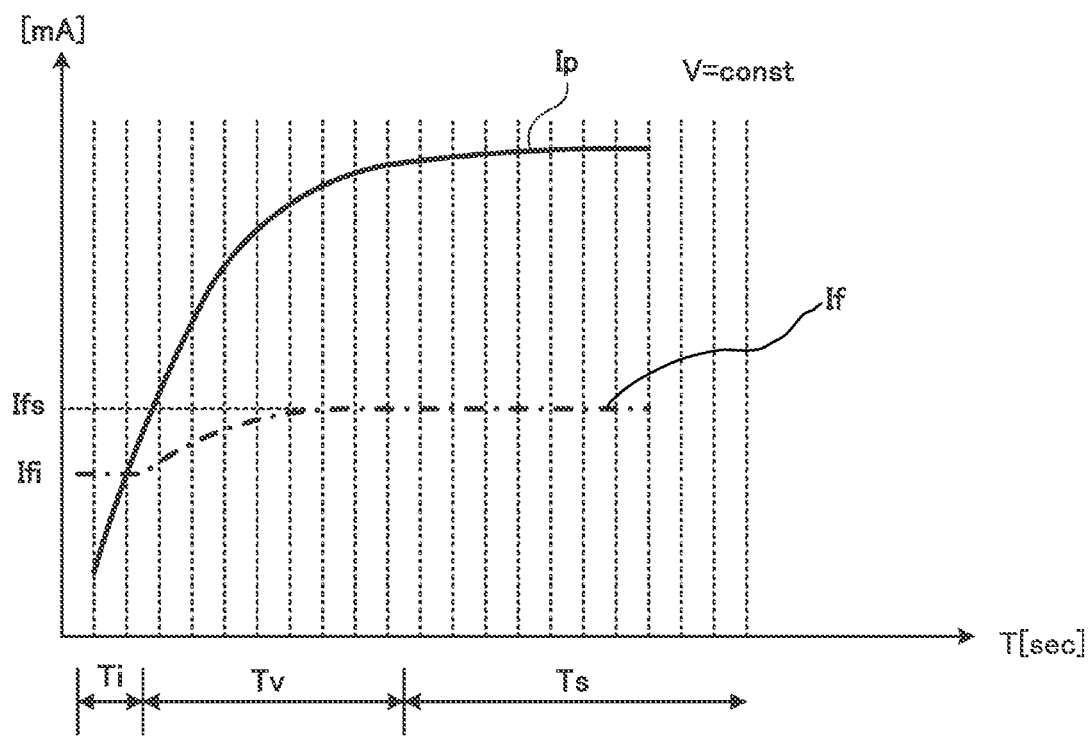
FIG. 3 is a graph showing relations between the filament current and the tube current in their rising up.

FIG. 3 is a graph showing relations between the filament current If and the tube current Ip with the tube voltage set at a certain constant value. In FIG. 3, the horizontal axis represents the time (t) that has elapsed since the initiation of radiography while the vertical axis expresses the filament current and the tube current. In FIG. 3, the initial value of the filament current used for activation is designated with "Ifi"; the stable value of the filament current when the tube current has become stable is designated with "Ifs"; and the initial period, the transition period, and the stable period of the activation are designated respectively with "Ti", "Tv", and "Ts".

In this embodiment, the initial value Ifi that has been used for the activation in this time of radiography (which may be referred to merely as "this time" in the following) is renewed with a new initial value Ifi to be used for the activation in a next radiography (which may be referred to merely as "next time" in the following). Incidentally, the initial value that has been used for the activation this time may be referred to as "this initial value" while the new initial value may be referred to as "next initial value". Here, this time and next time refer to the former and the latter in the chronological order of actions taken for executing a radiography or the like. This means that this initial value Ifi is updated to the next initial value Ifi whenever the initial value is used for a radiography or the like. As a result, despite the aging of the filament, the next initial value Ifi can be kept to an optimal value, and possibly, the work time required for a worker to adjust the initial values be shortened at the time of the adjustment, which is executed, for example, in a session of periodic performance testing. The next initial value Ifi is calculated based on its corresponding stable value Ifs, and how it is calculated will be described later.

As shown in FIG. 3, the tube current Ip during the activation changes (increases) throughout the initial period Ti and the transition period Tv and is stable during the stable period Ts. Also, the filament current If during the activation exhibits the initial value Ifi during the initial period Ti but increases after the initial period Ti, and then it is kept at a stable value Ifs during the stable period Ts.

FIG. 4 is a block diagram that illustrates the high voltage generator 15. As shown in FIG. 4, the high voltage generator 15, which generates a high voltage on a commercial AC power source 156, comprises a high voltage supply 151, which provides a tube voltage between the cathode 161 and the anode 162; a filament voltage supply 152, which produces a filament current on the basis of the commercial AC power source 156; a tube voltage detector 153, which detects the tube voltage being applied; a filament current detector 154, which detects the filament current; a tube current detector 155, which detects the tube current between the cathode 161 and the anode 162; and an X-ray tube controller 157.

The X-ray tube controller 157 controls the high voltage supply 151 in accordance with image-capturing conditions such that a predetermined tube voltage is applied. The X-ray tube controller 157 also controls the filament voltage supply 152 in such a way that the tube current detected by the tube current detector 155 is kept stable at the desired value specified for the tube current as an image-capturing condition. In other words, excesses and deficiencies in the tube current are detected by the tube current detector 155, and the filament current is controlled accordingly, to quickly stabilize the tube current, which otherwise tends to fluctuate during activation, at a desired value, by making use of the feedback of the filament current detected by the filament current detector 154 (refer to FIG. 3).

As shown in FIG. 2, the X-ray tube controller 157 comprises a storage 158, an initial value calculator 159, and an initial value estimator 159a.

The provision of the storage 158, the initial value calculator 159, the initial value estimator 159a, the display controller 90, and the display 100 enables the system to make a reduction in the work time required for adjusting the initial values, at which the filament current should flow through the cathode 161 of the X-ray tube 16 at activation.

(Storage)

Figure 5:
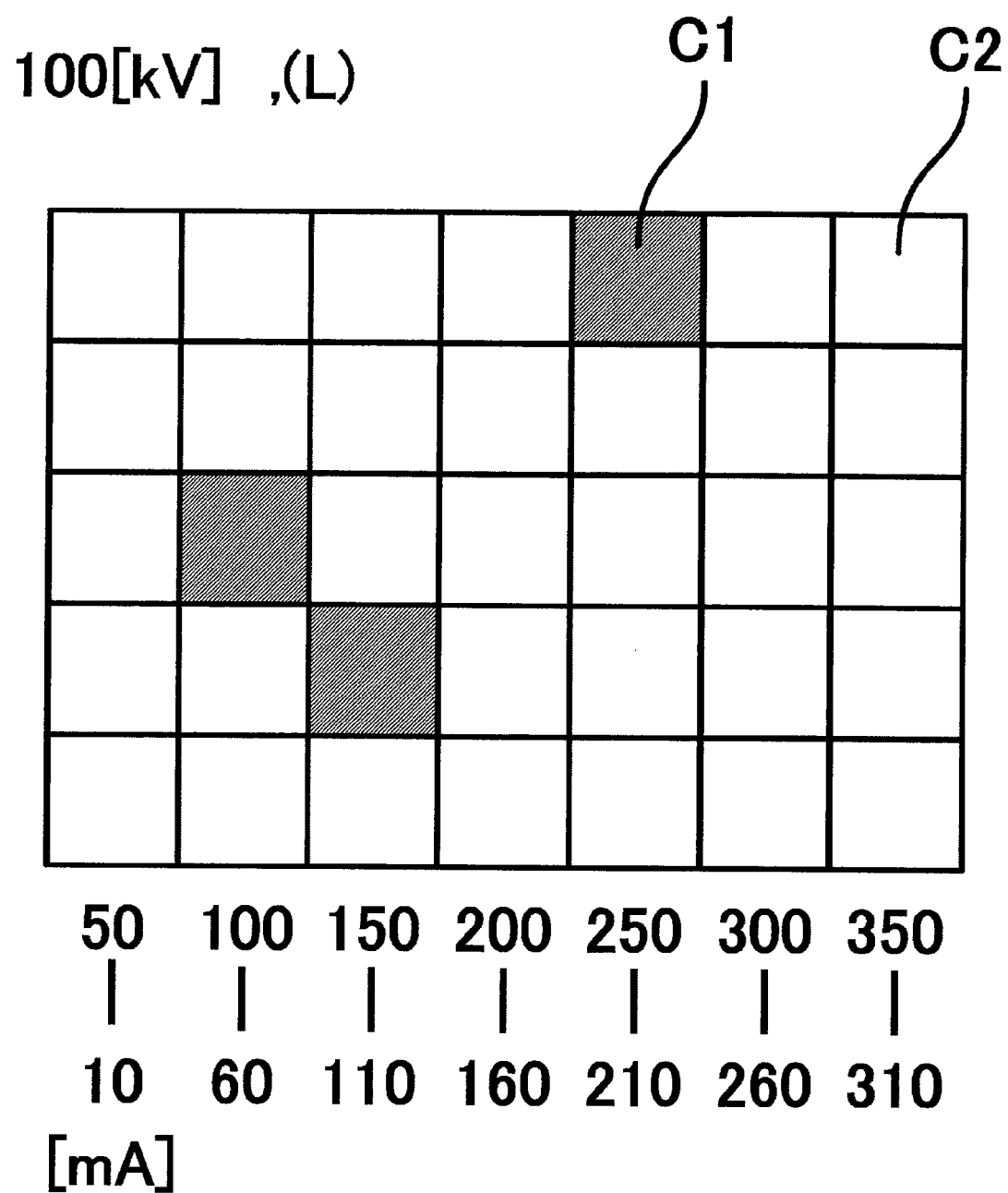
FIG. 5 is a drawing that represents a table.

FIG. 5 shows an example of a table that relates initial values and tube currents, which table is stored in the storage. In the present embodiment, the storage 158 stores eight tables that cover combinations of four values for the tube voltage (80, 100, 125, and 135 [kV]) and two focal spot sizes (Large and Small). (FIG. 5 is one example of the tables.) The table shown as an example in FIG. 5 is for a combination of a tube voltage of 100 [kV] with a focal spot size of large (L).

The tables, which are provided for each combination of the tube voltages and the focal spot sizes, correspond to a storage that stores the next initial values, the image-capturing conditions, and a radiographic history that includes radiographed dates.

As shown in FIG. 5, each cell of the table corresponds to a tube current increment of 10 [mA] in a range of 10 [mA]-350 [mA] and the next initial value Ifi is stored in a cell in relation to its corresponding tube current. In FIG. 5, the cells hatched in shade, for example C1, indicate that they are currently storing next initial values Ifi, and, for example, a hatched cell now stores a radiographed date of "2012.07.01". The information stored in the cell specifies the radiographed date; the table specifies the tube voltage and the focal spot size; and the position of the cell where the information is stored specifies the tube current.

As can be understood from the hatched cells shown in FIG. 5, the next initial values Ifi are stored respectively in relation to tube currents of 80 [mA], 120 [mA], and 250 [mA].

In FIG. 5, the cells that are not hatched, for example C2, are not currently storing next initial values Ifi. In this case, by taking a series of radiographs or the like under image-capturing conditions that are different from one another for the number of the cells that are not storing any next initial values, next initial values Ifi can be provided and stored to all the cells of the table (i.e., the table can be completed).

This method can take a long time to complete the table. For efficiently completing the table, the system estimates initial values Ifi for the combinations other than those between the tube currents and their corresponding initial values Ifi that are currently stored in cells, and the system stores the estimated initial values Ifi in the table. Here, the term "other next initial values" may be used for the estimated values. How the other next initial values Ifi are estimated will be described later.

By estimating the other next initial values Ifi that are not currently stored in cells, all the cells of the table can be provided and stored with their corresponding next initial values Ifi. The cells are related respectively to 10 [mA] increments of the tube current, and the initial values are adjusted for the respective 10 [mA] increments of the tube current. Consequently, at the time of a next adjustment, whatever value is selected for the tube current, the next initial value Ifi that exactly corresponds to the tube current can be applied, thus obviating the need for time-consuming adjustment.

Figure 6:
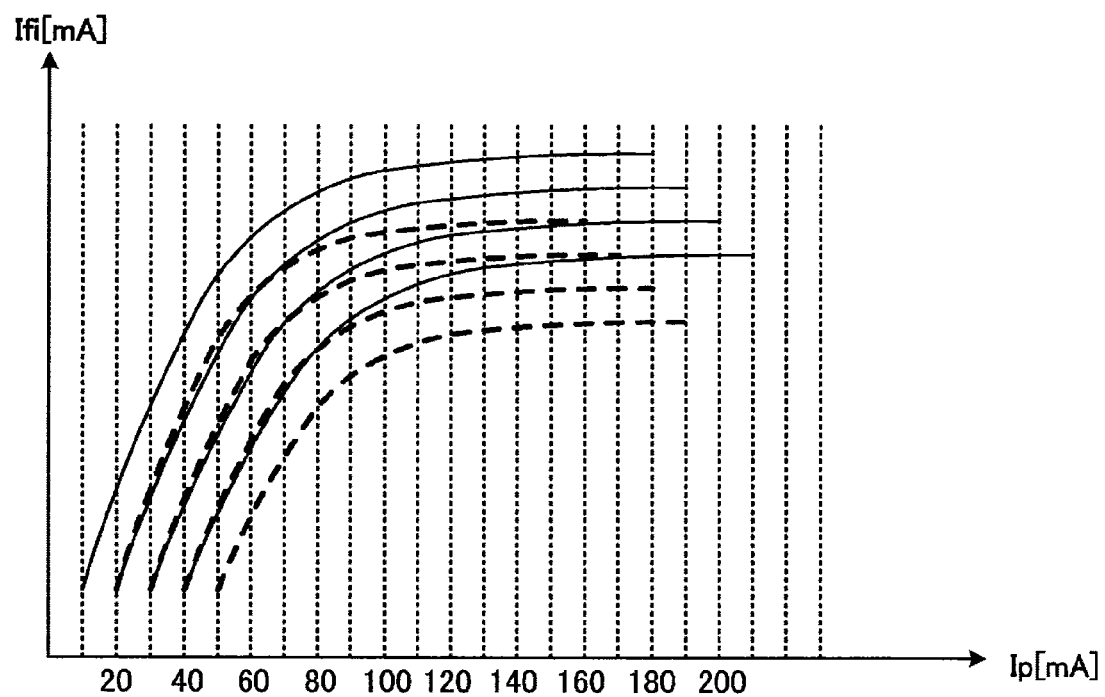
FIG. 6 is a graph showing relations between initial values and their corresponding tube currents.

FIG. 6 is a graph showing relations between initial values and tube currents. In FIG. 6, the horizontal axis describes tube currents Ip [mA] while the vertical axis describes next initial values Ifi [mA]. The vertical broken lines represent 10 [mA] increments of the tube current. This graph is prepared on the basis of the next initial values Ifi that are stored in cells and the next initial values Ifi that are estimated (i.e., both the initial values together fill all the cells of the tables). Four solid lines in FIG. 6 respectively correspond to tube voltages of 80, 100, 125, and 135 [kV] for the large (L) focal spot size while four broken lines respectively correspond to tube voltages of 80, 100, 125, and 135 [kV] for the small (S) focal spot size. Graphs as shown in FIG. 6 should be created eventually through radiography. For example, by using a graph (one of the eight) that corresponds to a predetermined tube voltage and a focal spot size, a next initial value is calculated for a tube current.

Incidentally, since initial values for every increment by 10 [mA] of the tube current are necessary for creating such a graph, initial values for filling the lacking points are calculated by linearly interpolating adjacent initial values. Graphs as shown in FIG. 6 are created on the basis of the initial values by using a well-known complementary method (e.g., Lagrangian method and spline method).

Such graphs as shown in FIG. 6 are stored in the storage 158 and are used in radiography or the like after the initial value adjustment if the tube current set as an image-capturing condition is not exactly at the 10 [mA] increments.

(Initial Value Calculator)

The initial value calculator 159 calculates a next initial value Ifi by subtracting a predetermined value δ from the stable value Ifs of this time of radiography. Incidentally, this predetermined value may be also referred to as "differential value".

Next initial value Ifi is expressed by the following equation.

$$Ifi = Ifs - \delta \quad (1)$$

Stable value Ifs is the value of the filament current at which the tube current flows stably (expressed as stable period Ts shown in FIG. 3). The stable value Ifs as information momentarily detected by the filament current detector 154 is sent together with the radiographic history (image-capturing conditions and radiographed date) from the X-ray tube controller 157 and is stored in the storage 158.

Differential value δ is a value that is specific to the image-capturing conditions of the X-ray CT system. In other words, it is a value that represents the influence of the system over such matters as from the control of the X-ray tube 16 to the actual shooting of X-rays. This value can be determined on the basis of empirical rules.

Differential value δ is expressed by the following equation.

$$\delta = f(V, Ip, S) \quad (2)$$

Here, V, Ip, and S represent respectively tube voltage, tube current, and focal spot size (large or small).

The differential value δ can be, therefore, calculated as a function of the tube voltage V, the tube current Ip, and the focal spot size S.

The next initial value Ifi is calculated by subtracting the predetermined value δ from the stable value Ifs. However, the present embodiment is not restricted to this way of calculation. The next initial value Ifi can be calculated by using the stable value Ifs and another predetermined value, which is, for example, a coefficient.

For example, the next initial value Ifi can be expressed by the following equation.

$$Ifi = \alpha \times Ifs \quad (3)$$

Here, α is a coefficient.

The coefficient α can be then expressed by the following equation.

$$\alpha = g(V, Ip, S) \quad (4)$$

Incidentally, the coefficient α may be calculated by the initial value calculator 159 in accordance with the equation (4) whenever the next initial value Ifi should be calculated, or it may be calculated in advance and be stored in the storage 158.

At the time of a radiography or the like, whenever X-rays are generated at the anode 162 in accordance with image-capturing conditions, the stable value Ifs is transmitted to the system controller 40, and the initial value calculator 159 calculates the next initial value Ifi based on the stable value Ifs transmitted. The next initial value Ifi calculated is then stored in the cell of the tube current on the table for the tube voltage and the focal spot size that corresponds to the calculated value.

(Initial Value Predictor)

In this embodiment, some next initial values Ifi are estimated for the cells that are not currently holding initial values, for the purpose of efficiently completing the tables as previously described.

Since the differential value is a value specific to the X-ray CT system, the correlation between the tube current and the stable value is also specific to the X-ray CT system. It is possible to estimate next initial values Ifi by applying the correlation.

Figure 7:
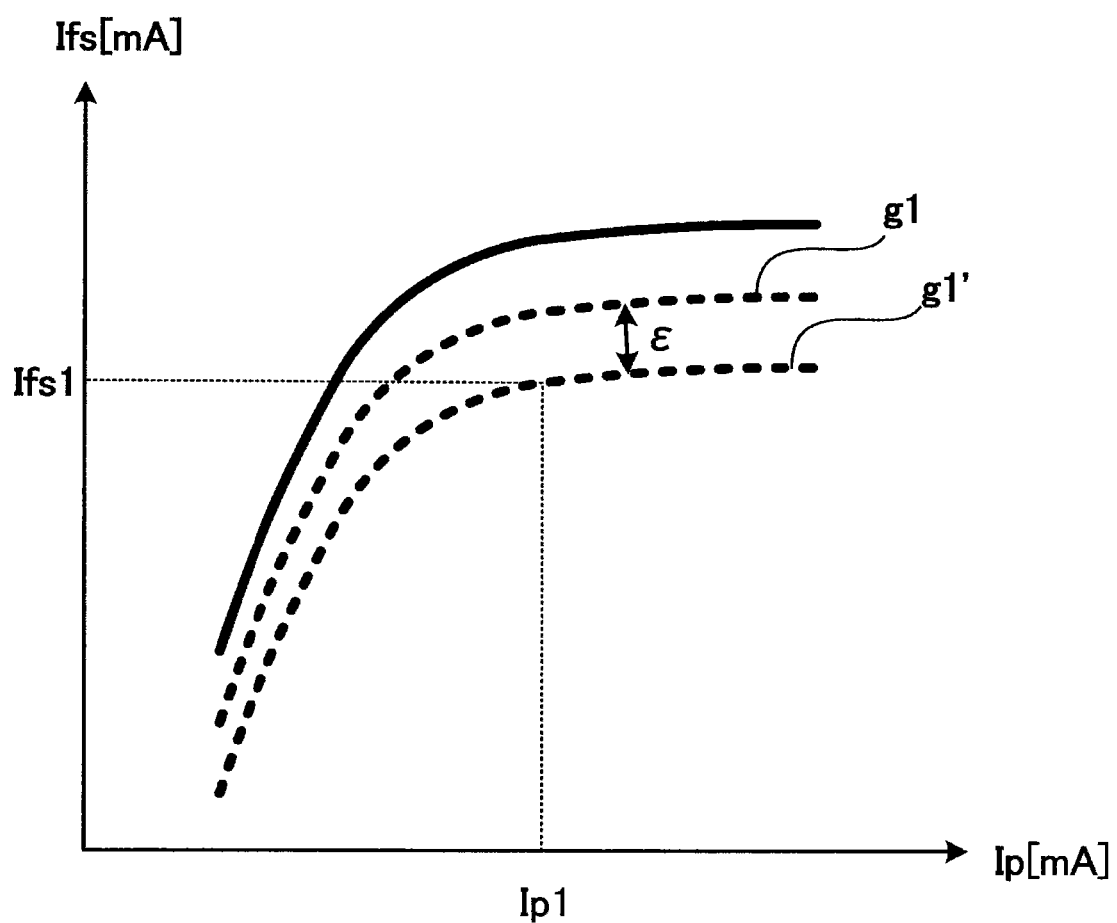
FIG. 7 is a graph showing correlations between tube currents and stable values.

FIG. 7 is a graph showing the correlation between the tube current and the stable value for a predetermined tube voltage and a focal spot size. In FIG. 7, the horizontal axis expresses values for the tube current Ip [mA] while the vertical axis expresses stable values Ifs [mA].

The initial value estimator 159a estimates a next initial value Ifi by using the correlation and the differential value, and the estimated initial value Ifi is stored in the cell of the table that corresponds to the estimation. Incidentally, the graph in FIG. 7 shows correlations (g1, g2, . . . , g8) each of which is for a specific tube voltage and a specific focal spot size, and the correlations described in this graph are applied with a shift that corresponds to the deviation ϵ that results from the aging of the filament. In the graph shown in FIG. 7, one of the eight correlation curves is drawn in a broken line and designated with "g1", and the one that is shifted from this curve is designated with "g1∝". By using this shifted curve "g1'", a stable value Ifs1 can be calculated for a tube current Ip1.

The next initial values Ifi calculated by the initial value calculator 159 and the next initial values Ifi estimated by the initial value estimator 159a are used to fill all the cells of the tables. Incidentally, the graph shown in FIG. 6 is created, based on the initial values Ifi, and stored in the storage 158.

(Display)

The display controller 90, upon receiving an operation executed with the operation unit 18, causes the display 100 to display next initial values Ifi stored in the tables. With the next initial values Ifi (optimal values) being displayed, there can be a reduction made in the work time required for the worker to adjust the initial values at the time of making adjustments, for example, during maintenance checks.

(Console)

As shown in FIG. 1 and FIG. 4, the console 30 comprises a system controller 40, a drive controller 45, a display controller 50, an input unit 60 and a display 70. The system controller 40 integrally controls the functions of the components provided in the console 30, and controls the gantry 10 and the patient table 20.

The system controller 40 receives the recorded next initial values Ifi from the gantry 10 and stores them in the table format as shown in FIG. 5 in the storage 41 as part of the radiographic history, which includes the image-capturing conditions at the time. The system controller 40, upon receiving a next-radiography instruction, refers to the radiographic history and the tables and sends image-capturing conditions that include a next initial value Ifi to the gantry 10.

A feature of the X-ray CT system of the first embodiment is that it includes the storage 158, the initial value calculator 159, the initial value estimator 159a, the display controller 90, and the display 100, which are provided on the side to the gantry 10 of the system for the purpose of reducing the time for making adjustments.

(Actions)

Now, a series of actions taken in a radiography or the like are explained with reference to FIG. 8, which is a flowchart showing a series of actions taken for a radiography or the like.

Figure 8:
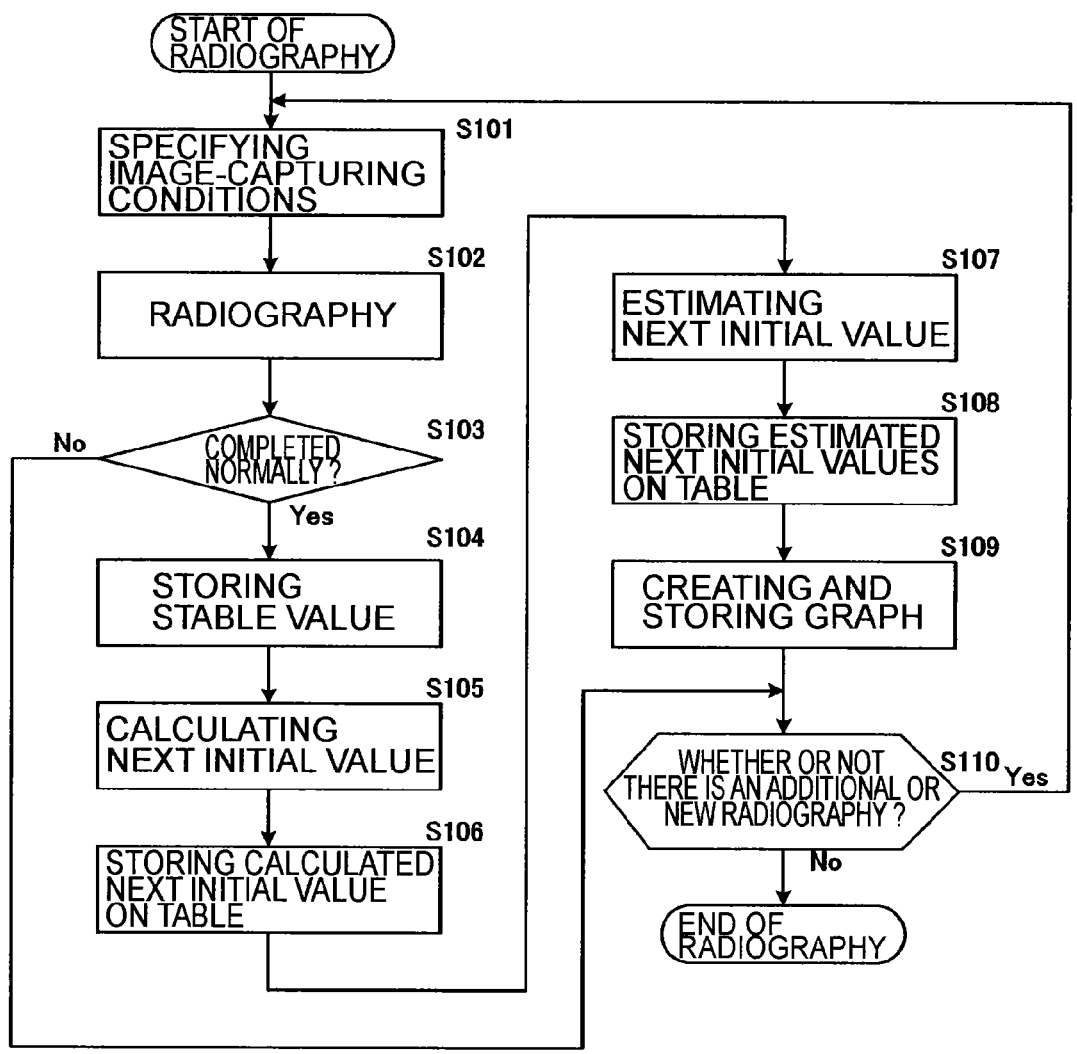
FIG. 8 is a flowchart showing a series of actions taken in radiography.

As shown in FIG. 8, in a radiography or the like, at first, the system controller 40 specifies image-capturing conditions (tube voltage, tube current, focal spot size, etc.) (S101). The system controller 40 reads out, from the radiographic history stored in the storage 158, the next initial value Ifi that has been applied for the same conditions as currently specified with a tube voltage, a tube current, and a focal spot size.

Then, a radiography or the like is executed (S102). In the radiography or the like, the X-ray tube controller 157 applies the filament current at the initial value Ifi, and the filament current at activation is controlled by making use of the feedback of the filament current detected by the filament current detector 154, so that the tube current detected by the tube current detector 155 will be at the specified value. As a result, the tube current is stabilized at a desired value, generating X-rays from the anode at a predetermined output.

After this, the X-ray tube controller 157 determines whether or not the radiography or the like has been completed normally (S103). If the determination results in that the radiography or the like has not been completed normally (S103: No), then the flow of control proceeds to step S110, where another determination is made of whether or not there is an additional or new radiography or the like to be performed.

If the determination results in that the radiography or the like has been completed normally (S103 Yes), then the system controller 40 stores, in the storage 158, the stable value of the filament current Ifs together with the radiographic history, which includes the image-capturing conditions (S104). At this stable value of the filament current, the tube current was stable at the specified tube-current value at the specified tube voltage.

Then, the initial value calculator 159 calculates a next initial value Ifi on the basis of the stable value Ifs and the above-mentioned differential value δ (S105).

After this, the X-ray tube controller 157 stores the calculated next initial value Ifi into the cell of the tube-current value on the table for the tube voltage and the focal spot size that corresponds to the calculation, the table being stored in the storage 158 (S106).

Then, the initial value estimator 159a estimates the other next initial values Ifi, which are for the tube-current values other than the one that has been calculated, on the basis of the correlations and differential values δ, which are shown in FIG. 7 (S107).

Then, the X-ray tube controller 157 stores the estimated, other next initial values Ifi into the cells that correspond to the tube-current values on the tables for which the estimation has been executed, with the tables being stored in the storage 158 (S108).

After this, the X-ray tube controller 157 creates a graph by using a well-known complementary method on the basis of the calculated next initial value Ifi and the estimated, other next initial values Ifi (refer to FIG. 6), and the X-ray tube controller stores the created graph in the storage 158 (S109).

Then, the system controller 40 determines whether or not there is an additional or new radiography or the like to be performed (S110). If the determination results in that there is an additional or new radiography or the like to be performed (S110: Yes), then the flow of control returns to step S101, where image-capturing conditions are specified. If the determination results in that there is no additional or new radiography or the like (S110: No), then the process of radiography or the like ends.

In the above-described process of radiography or the like, the created graph and the next initial values Ifi stored on the tables are used for a next radiography or the like.

Now, a series of actions taken for adjusting initial values are explained with reference to FIG. 9, which is a flowchart showing a series of actions taken for adjusting initial values.

Figure 9:
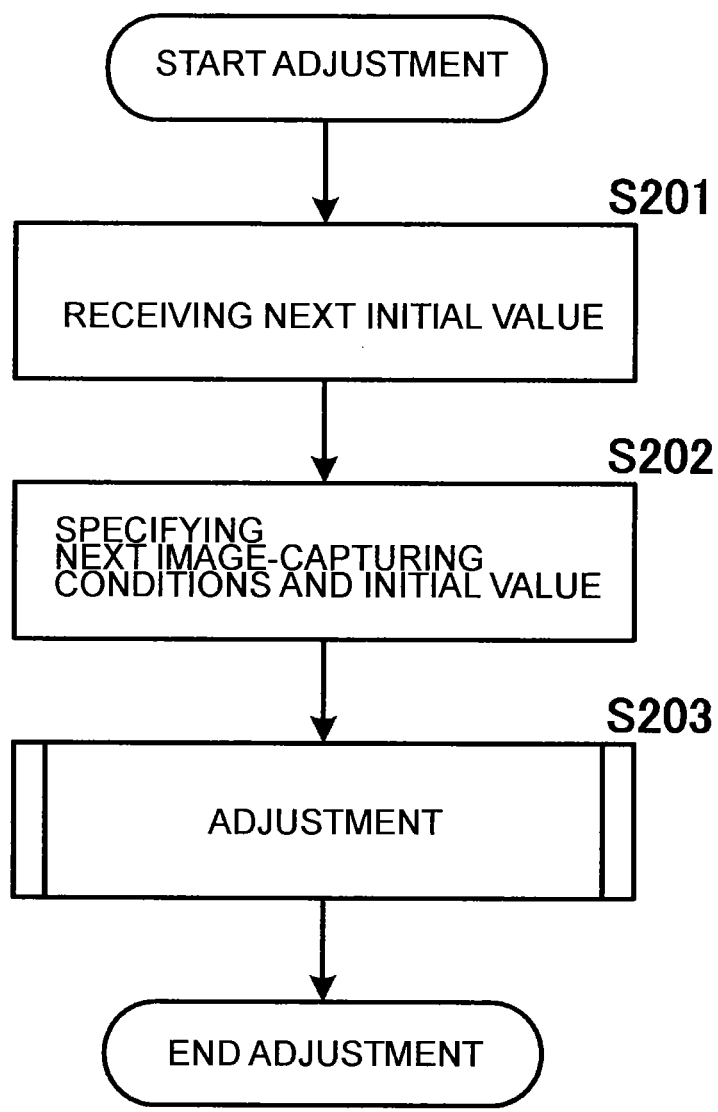
FIG. 9 is a flowchart showing a series of actions taken for adjusting an initial value.

As shown in FIG. 9, at first, the system controller 40 receives the next initial values Ifi from the gantry 10 (S201).

Then, the system controller 40 specifies next image-capturing conditions and an initial value Ifi (S202).

Then, it performs adjustment of the initial value Ifi (S203). In the adjustment of the initial value Ifi, a next initial value is calculated on the basis of the specified initial value Ifi (refer to FIG. 8 and to steps S101-S105). Following this, the system controller 40 creates a graph and stores it (refer to FIG. 8 and to steps S106-S109).

[Other Configurations]

Now, other configurations for the X-ray CT system are briefly described in reference to FIG. 1.

As shown in FIG. 1, the gantry 10 supports a revolving unit 11 in such a way that it revolves around the subject P. The revolving unit 11 comprises an X-ray tube 16 and an X-ray detector 17, which are disposed facing each other and are distanced respectively in opposing directions from the center of the revolution. As such, the gantry 10 supports the X-ray tube 16 that is capable of revolving around the subject P. The X-ray tube 16 irradiates X-rays on the subject P, so that the X-rays radiate within a flare angle in the rostrocaudal direction of the subject P (cone angle).

The gantry 10 comprises, in addition to these components, a rotary drive 12 and a data acquisition system 14.

The rotary drive 12 drives the revolving unit 11 to revolve around the center of the revolution.

The data acquisition system 14 comprises data acquisition elements, which are arranged in the same way as the array of X-ray detector elements of the X-ray detector 17. The data acquisition system 14 gathers detection signals as X-rays detected by the X-ray detector 17 in correspondence with data-acquisition signals received from the system controller 40. The gathered data are X-ray projection data.

The high voltage supply 151, upon receiving control signals from the X-ray tube controller 157, applies a high voltage to the X-ray tube 16. With the high voltage applied by the high voltage supply 151, the X-ray tube 16 generates and radiates a cone-like X-ray beam, which has a flare angle in the rostrocaudal direction (slicing direction, which is mentioned later) of the subject P, or a fan-like X-ray beam, which has a flare angle in channeling direction, which is mentioned later.

The X-ray detector 17 detects X-rays that have radiated from the X-ray tube 16 and passed through the subject P. The X-ray detector 17 is a two-dimensional X-ray detector 17 comprising X-ray detector elements arranged in an array in which the elements are aligned in two inter-orthogonal directions (slicing direction and channeling direction). The X-ray detector elements are arranged, for example, in 320 lines in the slicing direction and in 1,000 lines in the channeling direction.

Now, the patient table 20 is described with reference to FIG. 1. The patient table 20 comprises a couch top 21 and bed drives 22, 23, which moves the couch top 21 in accordance with instructions that are given with the operation unit 18.

The couch top 21 is mounted with the subject P. The couch top 21, with the subject P on it, is movable and driven in the rostrocaudal (horizontal) direction of the subject P.

The drive controller 45 sends, to the bed drive 22, control signals to move the couch top 21, which signals control the amount of displacement of the couch top 21 for every revolution of the revolving unit 11. The bed drive 22 moves the couch top 21 in the rostrocaudal direction of the subject P on the basis of the operation information (position of radiography) given with the operation unit 18.

In addition, the drive controller 45 sends to the bed drive 23 control signals to move the couch top 21. The bed drive 23 moves the couch top 21 in the up and down direction on the basis of the operation information given with the operation unit 18.

The drive controller 45 outputs gantry-control signals to the rotary drive 12 and data-acquisition-control signals to the data acquisition system 14, and the drive controller 45 gives instructions for starting a diagnostic session to the rotary drive 12 and to the bed drives 22, 23.

The console 30 includes a preprocessor 31, a reconstruction processor 32, and an image storage 33. The preprocessor 31 executes sensitivity correction and X-ray intensity correction on the X-ray projection data coming from the data-acquisition system 14. The reconstruction processor 32 reconstructs X-ray CT image data by executing a well-known method of back-projection processing on the X-ray projection data received from the preprocessor 31. The X-ray CT image data, which have been reconstructed, are stored temporarily in the image storage 33.

Variant Embodiment

In the above-mentioned embodiment, for adjustment of an initial value, a next initial value Ifi is calculated by specifying image-capturing conditions that include the initial value Ifi (refer to FIG. 9 and to S201-S203). The configuration is, however, not restricted to this. Initial value adjustment may be executed by receiving a signal that indicates the booting of the X-ray CT system.

With such a variant embodiment, the adjustment of the initial value is automatically executed at the starting of the apparatus. As a result, with an appropriate initial value that has been achieved at the beginning of radiographic work, stabilization of the tube current can be achieved within a very short time.

Second Embodiment

Now, a second embodiment of radiographic system is described with reference to FIG. 10. Incidentally, the parts of the configuration of the second embodiment that are the same as those of the first embodiment are designated with the corresponding identical numbers, and thereby the following description mainly concerns different parts of the configuration, leaving out description of the identical parts. Here, again, an X-ray CT system is described as an example of the radiographic system.

The first embodiment comprises a storage 158, an initial value calculator 159, an initial value estimator 159a, a display controller 90, and a display 100, which are provided on the side to the gantry 10 of the system for the purpose of making a work-time reduction.

(Console)

Figure 10:
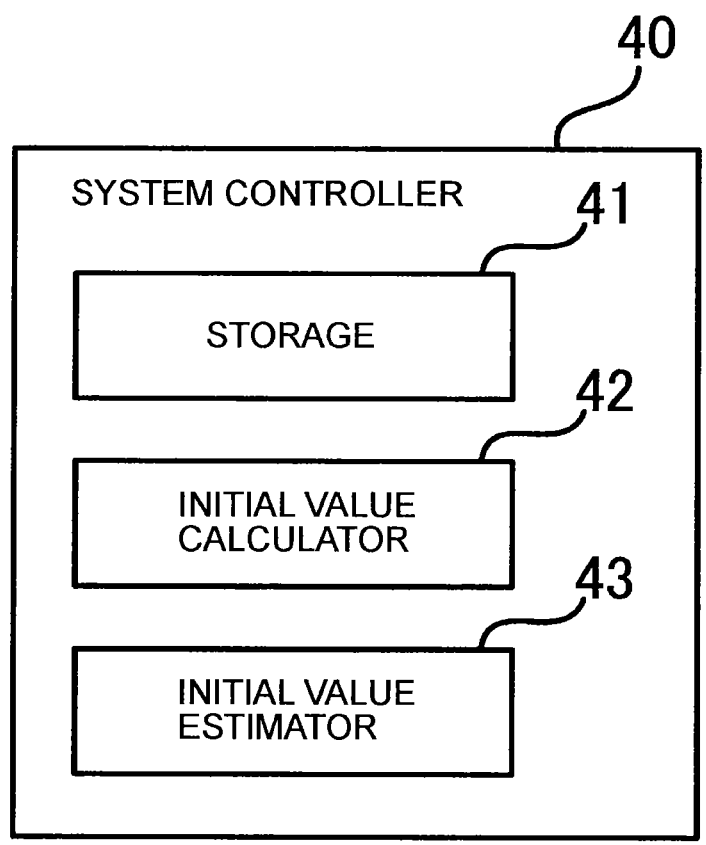
FIG. 10 is a block diagram showing a system controller as a second embodiment.

FIG. 10 is a block diagram showing a system controller 40 according to the second embodiment. As shown in FIG. 10, the second embodiment comprises a storage 41, an initial value calculator 42, an initial value estimator 43, a display controller 50 (refer to FIG. 1), and a display 70 (refer to FIG. 1), instead of the storage 158, the initial value calculator 159, the initial value estimator 159a, the display controller 90, and the display 100. These components are provided on the side to the console 30 of the system.

(System Controller)

The system controller 40 receives stable values Ifs from the gantry 10 side in a radiography or the like. The initial value calculator 42 calculates next initial values Ifi on the basis of the stable values Ifs. The initial value estimator 43 estimates next initial values Ifi. The system controller 40 creates a graph on the basis of the calculated next initial values Ifi and the estimated next initial values Ifi (refer to FIG. 6).

The storage 41 has tables on which next initial values Ifi are stored in correspondence with tube currents. The display 70 has the same functions as the display 100. The display controller 50 causes the display 70 to display next initial values Ifi.

With the second embodiment, stable values are received from the gantry 10 side regularly, for example, every month, and on the basis of the stable values for the one month, next initial values may be calculated collectively. Even with such an arrangement, the next initial values can be values that are appropriate for making a reduction in the work time required for adjusting the initial values.

Third Embodiment

Now, a third embodiment of radiographic system is described with reference to FIG. 10. Incidentally, the parts of the configuration of the third embodiment that are the same as those of the first embodiment are designated with the corresponding identical numbers. By leaving out description of the identical parts, the following description mainly deals with different parts of the configuration. Here, again, an X-ray CT system is described as an example of the radiographic system.

With the first embodiment, the adjustment of next initial values Ifi is carried out by a service engineer at the time of installation of the X-ray CT system or at the time of periodic performance testing (at the time of adjustment). This way of adjustment may be referred to as "non-automatic adjustment".

In contrast to this, with the third embodiment, the adjustment of next initial values Ifi is automatically executed.

Figure 11:
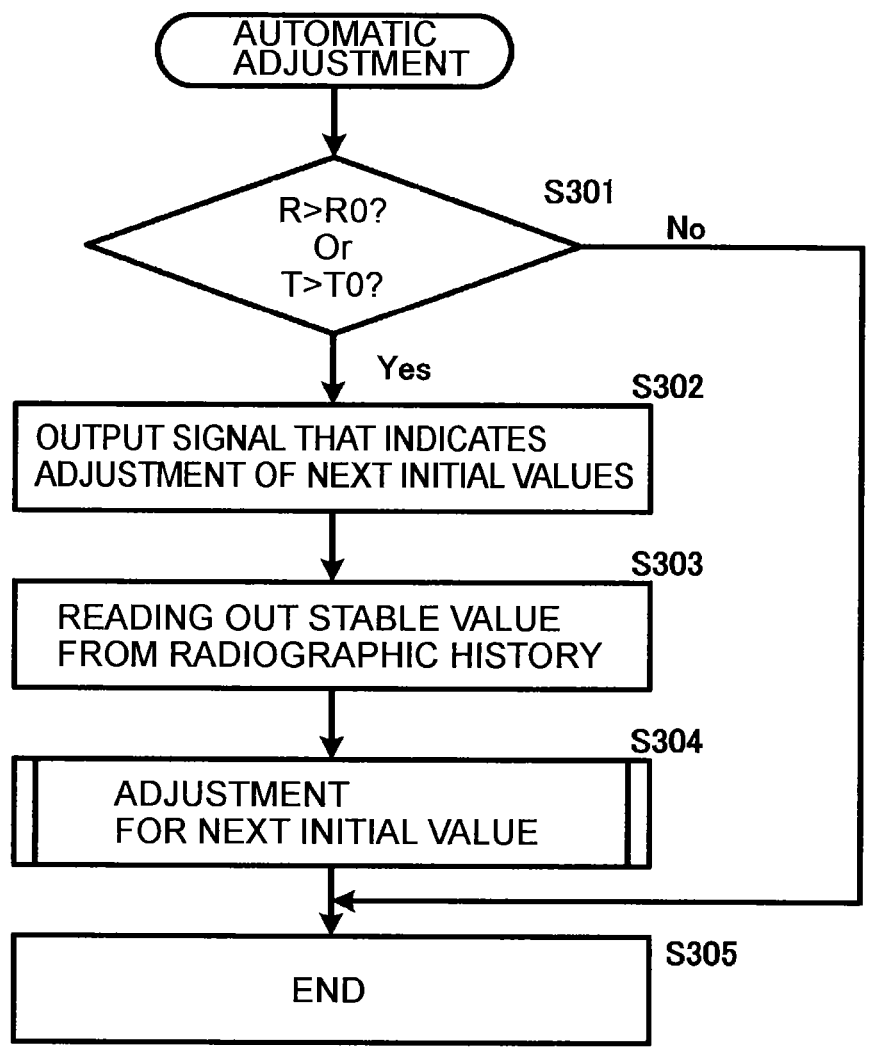
FIG. 11 is a flowchart showing a series of actions taken for automatically adjusting a next initial value with a third embodiment.

Now, a series of actions taken for automatically adjusting next initial values Ifi is explained with reference to FIG. 11, which is a flowchart showing a series of actions taken for automatically adjusting next initial values Ifi.

With the third embodiment, whenever a radiography is performed, the time and date, the initial value Ifi, the stable value Ifs, and the image-capturing conditions (tube current, tube voltage, and focal spot size) at the time are stored as radiographic history (log data) in the storage 41. In addition, the time that has elapsed since the last adjustment (either the automatic adjustment or the non-automatic adjustment) is counted. Furthermore, the number of radiographies taken is also counted.

Immediately after each radiography or at a predetermined time (e.g., 0:00 a.m.), the system controller 40 determines whether or not it is time to adjust the initial values Ifi (S301).

In determining the time for the adjustment of the initial values Ifi (S301), the counted elapsed time is compared with the predetermined time. Here, the elapsed time is designated with "T"; and the predetermined time, with "T0".

Furthermore, after the radiography, the number of radiographic executions is compared with the predetermined number of times. Here, the number of executions is designated with "R"; and the predetermined number of times, with "R0".

If the number of executions R exceeds the predetermined number of times R0 (R>R0), or the elapsed time T exceeds the predetermined time T0 (T>T0) (S301: Yes), then the system controller 40 outputs a signal that indicates an adjustment of next initial values Ifi (S302).

Incidentally, if the number of executions R has not exceeded the predetermined number of times R0 (R≤R0), and the elapsed time T has not exceeded the predetermined time T0 (T≤T0) (S301: No), then the system controller 40 judges that adjustment of initial values Ifi is unnecessary, and no adjustment is performed (S305).

Then, the system controller 40 reads out an initial value Ifi, a stable value Ifs, a tube voltage, a tube current and a focal spot size from the radiographic history (log data) (S303).

Then, adjustment is executed for a next initial value Ifi (S304).

Figure 12:
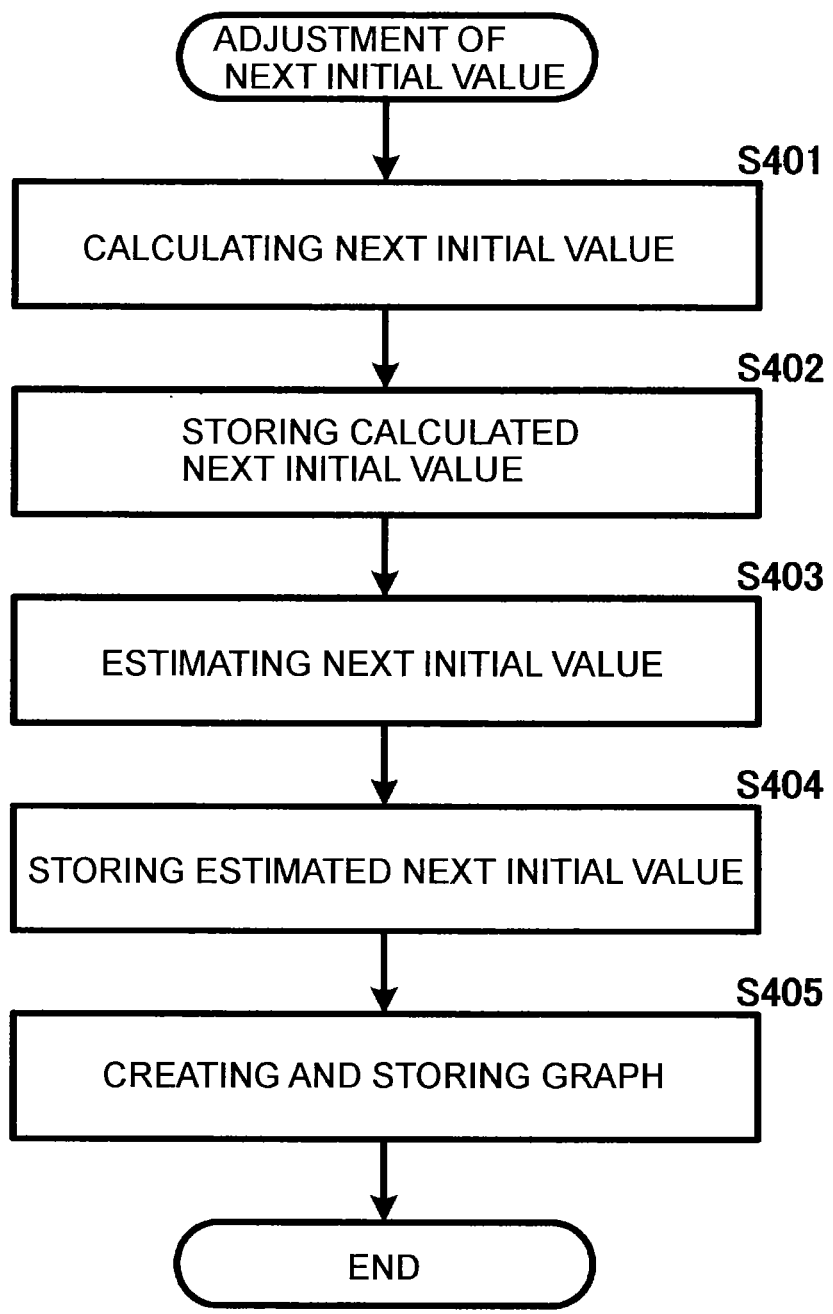
FIG. 12 is a flowchart showing a series of actions taken for adjusting next initial values.

Here, details of the adjustment made for the next initial values Ifi are explained with reference to FIG. 12, which is a flowchart showing a series of actions taken for adjusting a next initial value Ifi.

At first, a next initial value Ifi is calculated (S401).

Then, the calculated next initial value Ifi is stored into the cell of the tube-current value on the table for the tube voltage value and the focal spot size that corresponds to the calculation, the table being stored in the storage 41 (S402).

Then, other initial values Ifi are estimated (S403).

Then, the estimated, other next initial values Ifi are stored, respectively, into the cells of the respective tube-current values of the tables that correspond to the estimation, the tables being stored in the storage 41 (S404).

After this, a graph is created on the basis of the calculated next initial value Ifi and the estimated, other next initial values Ifi, by using a well-known complementary method (refer to FIG. 6), and the created graph is stored in the storage 41 (S405).

These steps S401-S405 are the same as steps S105-S109, which are executed with the first embodiment.

After the adjustment (S304) of the next initial values Ifi has been completed, the routine controlling the automatic adjustment ends (S305).

Incidentally, with the third embodiment, these steps S301-S305 are executed by the system controller 40, but they may be executed by another control unit (which can be the X-ray tube controller 157).

According to the third embodiment, the next initial values Ifi are adjusted automatically. This means that such an arrangement facilitates realization of a maintenance-free system.

Fourth Embodiment

Figure 13:
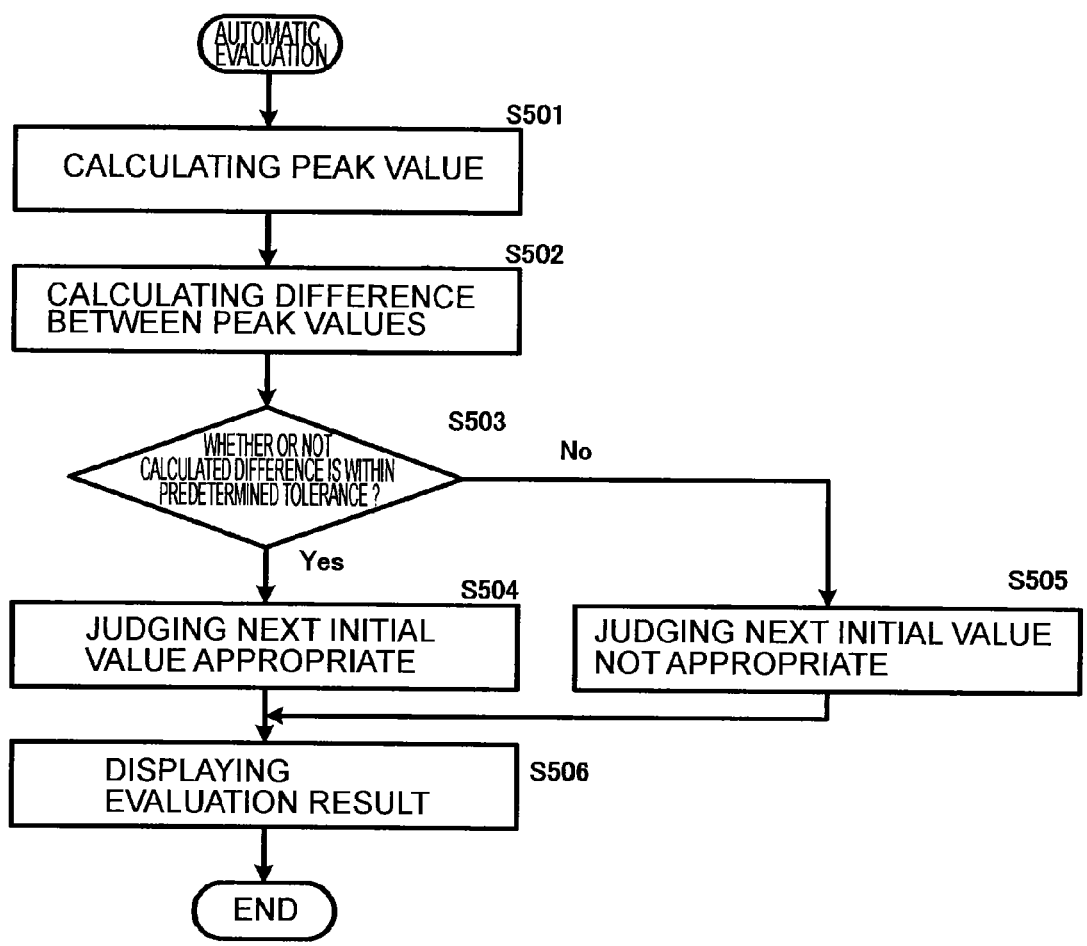
FIG. 13 is a flowchart showing a series of actions taken for evaluating the next initial values with a fourth embodiment.

Now, a fourth embodiment of radiographic system is described with reference to FIG. 13, which is a flowchart showing a series of actions taken for evaluating next initial values.

Incidentally, the parts of the configuration of the fourth embodiment that are the same as those of the first embodiment are designated with the corresponding identical numbers. By leaving out description of the identical parts, the following description mainly deals with different parts of the configuration. Here, again, an X-ray CT system is described as an example of the radiographic system.

With the first embodiment, the evaluation of the appropriateness of the next initial values Ifi is executed by a service engineer. This type of evaluation may be referred to as "non-automatic evaluation".

In contrast to this, with the fourth embodiment, the appropriateness of the next initial values Ifi is automatically evaluated.

At first, when a radiography using a next initial value Ifi is performed, the peak value of an overshoot and that of an undershoot of the tube current, which tends to fluctuate at activation, are calculated (S501). Then, the difference between the peak values of the overshoot and the undershoot is calculated (S502). After this, a determination is made of whether or not the calculated difference is within a predetermined tolerance (S503).

If the calculated difference is within the predetermined tolerance (S503: Yes), then the next initial value Ifi is judged appropriate (S504). On the other hand, If the calculated difference is not within the predetermined tolerance (S503: No), then the next initial value Ifi is judged not appropriate (S505).

After this, the evaluation result is displayed on the display (S506). The system controller 40 may execute these steps S501-S506, or another control unit that is provided in the system (which can be the X-ray tube controller 157) may execute them.

Incidentally, if the next initial value Ifi is judged not appropriate, then a second adjustment is made for the next initial value Ifi. The second adjustment may be an automatic adjustment (steps S301-S305, which are mentioned above), or it may be a non-automatic adjustment carried out by a service engineer.

According to the fourth embodiment, since the evaluation whether or not the next initial value Ifi is appropriate is automatically executed, the evaluation of the next initial value Ifi is performed objectively. As a result, the initial value Ifi that has been acquired is both comparatively appropriate and objective. Furthermore, the combination of automatic evaluation and automatic adjustment of the next initial value Ifi can facilitate the realization of a maintenance-free system.

With the fourth embodiment, the difference between the peak values of an overshoot and an undershoot is used for the determination whether the difference is within the predetermined tolerance or not at step S503. However, whether or not the peak value of an overshoot has exceeded the tolerance can be determined instead, and if it has, then the next initial value Ifi may be judged not appropriate. Equally, whether or not the peak value of an undershoot has gone out of the tolerance can be determined, and if it has, then the next initial value Ifi may be judged not appropriate.

Incidentally, concerning the present embodiment, the storage 158, the initial value calculator 159, the initial value estimator 159a, the display controller 90, and the display 100 are all explained as components that are applied to an X-ray CT system. The present embodiment is, however, not restrained to such a configuration. It can be applied to any X-ray generator that has an X-ray tube 16 comprising an anode and a cathode including a filament, and to any X-ray apparatus that is equipped with such an X-ray generator.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

DESCRIPTIONS OF NUMBERED PARTS 10, gantry;
11, revolving unit;
12, rotary drive;
14, data-acquisition system;
15, high voltage generator;
158, storage;
159, initial value calculator;
159a, initial value estimator;
16, X-ray tube;
17, X-ray detector;
18, operation unit;
20, patient table;
30, console;
40, system controller;
45, drive controller;
50, display controller;
60, input unit;
70, display;
90, display controller;
100, display.

What is claimed is:

1. A radiographic system that performs a radiography with X-rays generated from an X-ray tube based on image-capturing conditions that include an X-ray focal spot size, a tube current, and a tube voltage to be applied between an anode and a cathode in the X-ray tube, comprising:
an X-ray tube controller configured to control a filament current flowing through a filament of the cathode of the X-ray tube for stabilizing the tube current at a desired value, the tube current otherwise tending to fluctuate at activation;
an initial value calculator configured to calculate an initial value for the filament current that is to be applied at next activation, based both on a stable value of the filament current while the tube current has been stable and on the image-capturing conditions at the time; and
a storage configured to store the calculated initial value, the image-capturing conditions, and a radiographic history that includes radiographed dates.

2. A radiographic system according to claim 1, wherein the initial value calculator calculates the initial value by using the stable value and a predetermined value.

3. A radiographic system according to claim 2, wherein
the storage has tables prepared for combinations of various tube voltage values and focal spot sizes; and
the calculated initial value is stored on the tables in combination with a tube-current value at the time.

4. A radiographic system according to claim 3, further, comprising an initial value estimator configured to estimate initial values by using the predetermined value and predetermined correlations between tube-current values and filament-current stable values, the initial values estimated here being other than the initial value that has been calculated and stored in combination with its corresponding tube-current value, of all the initial values that can be applied at next activation; and
the estimated initial values are then stored in combination with their corresponding tube-current values on the tables.

5. A radiographic system according to claim 4, further comprising:
a gantry comprising the X-ray tube, the X-ray tube controller, the storage, the initial value calculator, and the initial value estimator; and
a console configured to, upon receiving an instruction of image-capturing conditions, send an initial value together with the image-capturing conditions to the X-ray tube controller;
wherein after a radiography has been performed in accordance with the instruction received, which includes the image-capturing conditions, the initial value calculator calculates a next initial value, and the initial value estimator estimates other next initial values.

6. A radiographic system according to claim 4, further comprising:
- a gantry comprising the X-ray tube, the X-ray tube controller, the storage, the initial value calculator, and the initial value estimator; and
- a console configured to send a start-up signal to the X-ray tube controller;
- wherein the initial value calculator, upon receiving the signal, calculates a next initial value; and the initial value estimator estimates other next initial values.

7. A radiographic system according to claim 4, further comprising:
- a gantry comprising the X-ray tube and the X-ray tube controller; and
- a console configured to include the storage, the initial value calculator, and the initial value estimator, and the console also configured both to send image-capturing conditions to the X-ray tube controller and to receive the stable value from the gantry;
- wherein the initial value calculator, upon receiving the stable value, calculates a next initial value, and the initial value estimator estimates other next initial values.

8. A radiographic system that performs a radiography with X-rays generated from an X-ray tube based on image-capturing conditions that include an X-ray focal spot size, a tube current, and a tube voltage to be applied between an anode and a cathode in the X-ray tube, comprising:
- an X-ray tube controller configured to control a filament current flowing through a filament of the cathode of the X-ray tube for stabilizing the tube current at a desired value, the tube current otherwise tending to fluctuate at activation;
- an initial value calculator configured to, upon receiving a signal that instructs an initial value adjustment for the filament current to be applied at next activation, calculate an initial value, based on a stable value of the filament current while the tube current has been stable and on the image-capturing conditions applied at the time; and
- an initial value estimator configured to, upon receiving the signal, which instructs an initial value adjustment, estimate initial values by using a predetermined value and predetermined correlations between tube-current values and filament-current stable values, the initial values estimated being other than the initial value that has been calculated in combination with its corresponding tube-current value, of all the initial values that can be applied at next activation; and
- a storage configured to store the calculated initial value, the estimated initial values, the image-capturing conditions, and a radiographic history that includes radiographed dates.

9. A radiographic system according to claim 8, further comprising:
- a determiner configured to determine whether or not the tube current, which tends to fluctuate at activation, is within a predetermined tolerance; and
- a display configured to display a result of the determination executed by the determiner.

* * * * *